US008632982B2

(12) United States Patent
Hu et al.

(10) Patent No.: US 8,632,982 B2
(45) Date of Patent: Jan. 21, 2014

(54) BIOMARKERS FOR LIVER INJURY

(75) Inventors: Zhiyuan Hu, Seattle, WA (US);
Christopher Lausted, Seattle, WA (US);
Leroy Hood, Seattle, WA (US)

(73) Assignee: Institute for Systems Biology, Seattle, WA (US)

( * ) Notice: Subject to any disclaimer, the term of this patent is extended or adjusted under 35 U.S.C. 154(b) by 154 days.

(21) Appl. No.: 12/785,279

(22) Filed: May 21, 2010

(65) Prior Publication Data

US 2010/0298161 A1 Nov. 25, 2010

Related U.S. Application Data

(60) Provisional application No. 61/180,402, filed on May 21, 2009.

(51) Int. Cl.
*G01N 33/53* (2006.01)
*C07K 16/00* (2006.01)

(52) U.S. Cl.
USPC ........................................ 435/7.1; 530/387.1

(58) Field of Classification Search
None
See application file for complete search history.

(56) References Cited

U.S. PATENT DOCUMENTS

| 7,590,493 | B2 * | 9/2009 | Mendrick et al. | 702/19 |
| 2006/0228327 | A1 | 10/2006 | Proudfoot et al. | |
| 2006/0246489 | A1 * | 11/2006 | Svetlov et al. | 435/6 |
| 2007/0078088 | A1 | 4/2007 | Hunter et al. | |
| 2009/0053207 | A1 | 2/2009 | Al Hendy | |

FOREIGN PATENT DOCUMENTS

JP   2007006800 A  * 1/2007

OTHER PUBLICATIONS

Newton et al., Liver Proteome Analysis in a Rodent Model of Alcoholic Steatosis; J Proteome Research, vol. 8, No. 4, pp. 1663-1671, 2009.*
Fella et al., Use of two-dimensional gel electrophoresis in predictive toxicology: Identification of potential early protein biomarkers in chemically induced hepatocarcinogenesis; Proteomics, vol. 5, pp. 1914-1927, 2005.*
Collins et al. The application of genomic and proteomic technologies in predictive, preventive and personalized medicine; Vascular Pharmacology, vol. 45, pp. 258-267, 2006.*
Gressner et al., Biomarkers of liver fibrosis: Clinical translation of molecular pathogenesis or based on liver-dependent malfunction tests; Clinica Chimica Acta vol. 381 pp. 107-113, 2007.*
Zhou et al., Serum Tumor markers of HCC; World Journal of Gastroenterology, vol. 12, No. 8, pp. 1175-1181, 2006.*
Wassaf et al., High-throughput affinity ranking of antibodies using surface Plasmon resonance microarrays; Analytical Biochemistry, vol. 351, pp. 241-253, 2006.*
Moller et al., Soluble CD163 from activated macrophages predicts mortality in acute liver failure; Journal of Hepatology, vol. 47, pp. 671-676, 2007.*
Spano et al., Changes of the Hepatic Proteome in Hepatitis B-Infected Mouse Model at Early Stages of Fibrosis; J Proteome Res, vol. 7, pp. 2642-2653, 2008.*
Kingsmore et al., Multiplexed protein measurement: technologies and applications of protein and antibody arrays; Nature Reviews Drug Discovery; Advanced Online Publication published Mar. 17, 2006, pp. 1-11.*
Translation of Nojima et al., JP 2007-006800 A; Machine translation from JPO downloaded May 21, 2013.*
International Search Report for PCT/US10/35829, mailed on Jul. 12, 2010, 2 pages.
Written Opinion of the International Searching Authority for PCT/US10/35829, mailed on Jul. 12, 2010, 4 pages.

* cited by examiner

*Primary Examiner* — Celine X Qian
*Assistant Examiner* — Addison D Ault
(74) *Attorney, Agent, or Firm* — Morrison & Foerster LLP

(57) ABSTRACT

Fourteen markers not previously known to be associated with liver injury have been identified. Methods to diagnose a subject for liver injury using these markers are described.

9 Claims, 4 Drawing Sheets

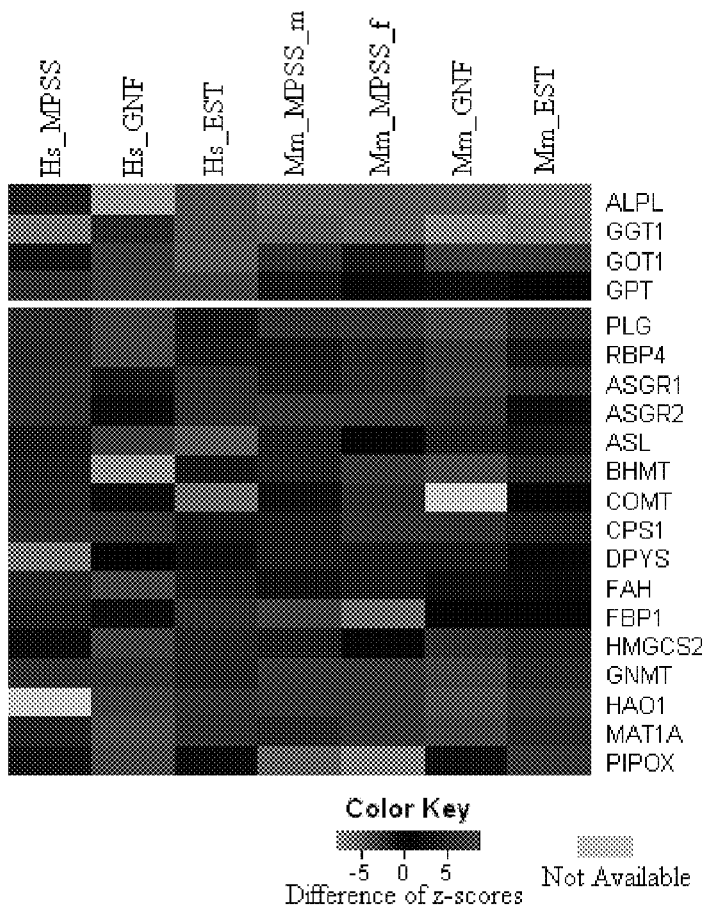

Current markers:
GPT-Alanine aminotransferase (ALT)
GOT1-Aspartate aminotransferase (AST)
ALPL-Alkaline Phosphatase (AP)
GGT1-Gamma Glutamyl Transpeptidases (GGT)

New panel:
PLG-Plasminogen
RBP4-Retinol-binding protein 4
ASGR1-Asialoglycoprotein receptor 1
ASGR2-Asialoglycoprotein receptor 2
ASL-Argininosuccinate lyase (*)
BHMT-Betaine--homocysteine S-methyltransferase 1
COMT-Catechol-O-methyltransferase
CPS1-Carbamoyl-phosphate synthetase 1 (*)
DPYS-Dihydropyrimidinase
FAH-Fumarylacetoacetate hydrolase
FBP1-Fructose-1,6-bisphosphatase 1
HMGCS2-3-hydroxy-3-methylglutaryl coenzyme A synthase
GNMT-Glycine N-methyltransferase
HAO1-Hydroxyacid oxidase 1
MAT1A-Methionine adenosyltransferase 1
PIPOX-L-pipecolic acid oxidase
(*) not novel

Figure 1

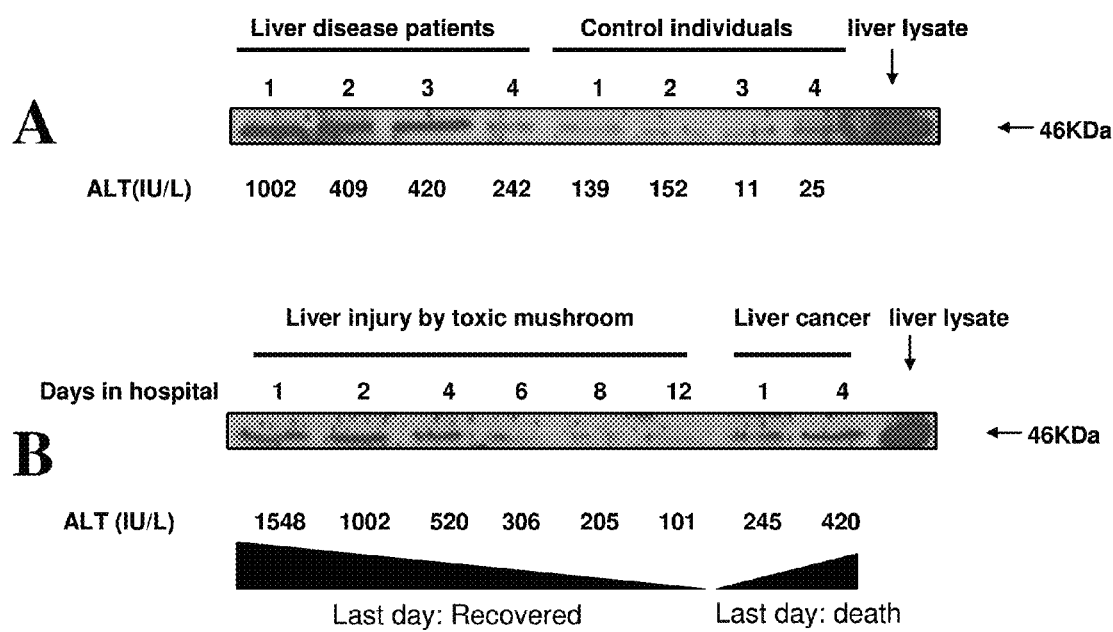
Figure 4(A-B)

BIOMARKERS FOR LIVER INJURY

RELATED APPLICATION

This application claims benefit of U.S. application Ser. No. 61/180,402 filed May 21, 2009. The contents of this document are incorporated herein by reference.

STATEMENT OF RIGHTS TO INVENTIONS MADE UNDER FEDERALLY SPONSORED RESEARCH

This work was supported in part by a grant from the Department of Defense, grant No. W911SR-07-C-0101. The U.S. government has certain rights in this invention.

TECHNICAL FIELD

The invention relates to biomarkers secreted into the circulatory system in subjects experiencing diseased or injured livers. More particularly, the invention concerns methods to assess subjects for liver injury using one or more of the biomarkers of the invention.

BACKGROUND ART

There are a number of biomarkers of liver injury available in the art, including, for example, alanine transaminase (ALT), aspartate transaminase (AST), alkaline phosphatase (ALP), gamma-glutamyl transferase (GGT) and lactate dehydrogenase (LDH). Liver injury is a major contributor to morbidity in the U.S. and elsewhere and can be caused by many factors. One significant factor is the ingestion of acetaminophen at dosage levels above those recommended. Additional liver injuries are caused by ischemia or reperfusion, abdominal surgery, hemorrhagic and septic shock, other trauma to the abdomen, liver transplantation, and liver cancer.

The known markers have not been entirely satisfactory, either because they are not sufficiently sensitive or not sufficiently specific or both. The present invention remedies this by introducing 14 novel and sensitive markers that may be used alone or in combinations as panels or in combination with known biomarkers.

Any documents cited herein are incorporated by reference in their entirety, as are any amino acid sequences or nucleotide sequences that are referenced and known in the art. Thus, the proteins listed as markers and the nucleotide sequences encoding them are hereby incorporated by reference.

DISCLOSURE OF THE INVENTION

In one aspect, the invention is directed to a method to identify a subject having a liver injury which method comprises analyzing a biological fluid obtained from said subject for the presence, absence or amount of an mRNA or a protein selected from the group consisting of asialoglycoprotein receptor 1 (ASGR1), asialoglycoprotein receptor 2 (ASGR2), betaine-homocysteine S-methyltransferase 1 (BHMT), catechol-O-methyltransferase (COMT), dihydropyrimidinase (DPYS), fructose, fructose-1-6-bisphosphatase 1 (FBP1), fumarylacetoacetate hydrolase (FAH), glycine-N-methyltransferase (GNMT), hydroxyacid oxidase 1 (HAO1), 3-hydroxy-3-methylglutaryl-coenzyme A synthase 2 (HMGCS2), L-pipecolic acid oxidase (PIPOX), and methionine adenosyltransferase 1 (MAT1A), wherein an increased level of one or more of these mRNAs or proteins in the biological fluid indicates liver injury, or assessing the presence or absence or amount of mRNA encoding, or protein which is, plasminogen (PLG) or retinal binding protein 4 (RBP4) wherein a decreased level of this mRNA or protein in the biological fluid indicates the presence of liver injury.

In the method of the invention, any of the foregoing markers may be assessed in combination with one or more of the others, and/or in combination with additional markers already known in the art, such as ALT, AST, and the like.

The level of these proteins may be assessed by a variety of methods known in the art, including Western blot, immunoassay, and the like. In one embodiment, a microarray of antibodies directed against a multiplicity of the foregoing markers including, if desired, antibodies to known markers may be used. Western blot would permit analysis by size, and in addition, other immunoassay methods, including homogeneous methods, lateral flow assays, and the like may be employed. The levels of mRNA in fluids can also be studied by art-known methods such as reverse transcriptase PCR (RT-PCR), Northern blot, and the like.

The invention also includes kits for analysis of one or more of the new markers set forth above.

BRIEF DESCRIPTION OF THE DRAWINGS

FIG. 1 shows the level of expression of genes encoding various proteins at the RNA level as determined in three platforms assessing expression of various genes in human and murine tissues.

FIG. 4A compares the concentration of FAH in serum of human liver disease patients with the levels in serum of control individuals. These results are correlated with results obtained by the standard ALT test for liver damage.

FIG. 4B shows the time course of detection levels of FAH in the serum of a recovering liver disease patient compared to a patient with liver cancer, also correlated with results obtained by the standard ALT test for liver damage.

MODES OF CARRYING OUT THE INVENTION

Figure 2:
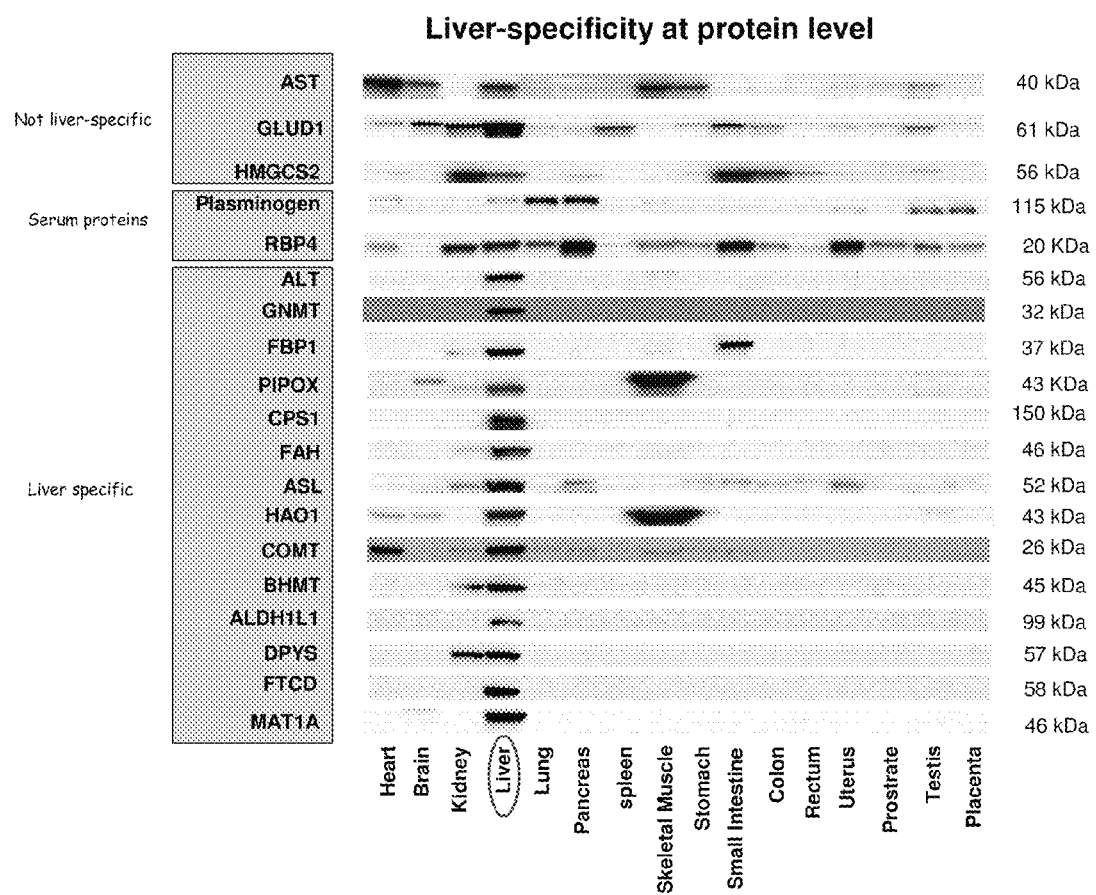
FIG. 2 shows the results of a Western blot determination of the expression of various genes in liver and 15 additional normal human tissues.

Fourteen new protein biomarkers for liver damage detectable in the circulation have been identified; 12 of them show elevated concentrations in for example, serum when the subject is afflicted with liver injury and two of them show reduced levels. These markers may be used individually, or in combination with each other and/or in combination with known markers to improve diagnosis and prognosis in subjects suspected of harboring liver injury. Proper assessment of such injury will inform treatment protocols.

The biological fluid is most conveniently a blood fraction, in particular, serum or plasma, but can also be saliva, urine or semen. Methods for obtaining suitable samples of these fluids are routine.

The assessment of protein concentration is also within ordinary skill One commonly used form is an immunoassay, including lateral flow assays in various formats, homogeneous immunoassays, and the like. In addition, microarray substrates containing a multiplicity of antibodies can streamline forms of the assay where a multiplicity of markers is assessed. A convenient protocol involves the use of surface plasmon resonance to detect the binding of relevant proteins to antibodies on the substrate.

Microarrays can also be used with labeled proteins, such as fluorescent or luminescent samples, or with a label-free detection method. Surface Plasmon Resonance (SPR) imaging is one such method to detect the binding of relevant proteins to antibodies on the substrate. SPR imaging monitors protein-binding microarrays in a manner that is label-free, real-time, and reusable. Since it is label-free, the process is fast, economical, and free of labeling biases. The real-time aspect allows for binding kinetics to be observed and for the quality of the antibody-protein interaction to be evaluated. As the arrays are reusable, a large number of samples can be processed on the same sensor chip efficiently.

In general, SPR techniques detect the changes in the effective refractive index (the thickness of the adsorbed layer) near the SPR-active surface. When polarized, collimated light is reflected from the active surface at an angle greater than the critical angle, incident photons are coupled into surface plasmons, leading to a decrease in the reflected light intensity. Binding events at predefined positions increase the local refractive index, changing the reflectance pattern across the surface. This pattern is recorded in real-time using an imager such as a CCD camera. Protein concentrations in a sample solution are thus determined by monitoring the change in refractive index caused by interaction of capture molecules on the surface with the targeted proteins.

Alternatively or in addition, assessment by quantitative mass spectrometry may be used. This method employs a mass spectrometer to detect gas phase ions. Mass spectrometers employ an ionization source and a mass analyzer. Examples of mass analyzers are time-of-flight, magnetic sector, quadrupole filter, ion trap, ion cyclotron resonance, and electrostatic sector. Quantitative protein analysis of complex biofluids is typically performed by a tandem mass spectrometer (MS-MS)—a type of instrument that has more than one analyzer (and usually two in practice). MS-MS produces structural information by fragmenting specific sample ions for identification. This information is then pieced together to generate structural information regarding the original molecule and to detect targeted proteins based on their characteristic fragmentation patterns.

Quantitative proteomic analysis can be achieved by the use of the mass spectral method designated Multiple Reaction Monitoring (MRM). In MRM MS-MS, both of the analyzers are static as user-selected specific ions are transmitted through the first analyzer and target-specific fragments arising from these ions are measured by the second analyzer. The selection and identification steps are enabled by the use of well-characterized, labeled calibration peptides. This results in a method with both very high measurement specificity and sensitivity.

Many of the art-known methods to detect proteins employ immunoreaction with antibodies. "Antibodies" as used in the present case, refers not only to intact monoclonal or polyclonal antibodies, but also the immunospecific fragments thereof, including single-chain antibodies and recombinantly produced antibodies in general. As an alternative to antibodies, any specific binding partner to the protein to be detected could also be employed. For example, compounds that bind the proteins as suicide substrates might be employed. Alternatively, as many of the markers are themselves enzymes, enzymatic assays for their activity could also be used to detect them.

Also available is assessment by Western blot which permits the simultaneous determination of a number of the markers depending on size. FIG. 2 shows the molecular weights of the markers of the invention.

The levels of mRNA in biological fluids can also readily be assessed by a variety of methods. Microarrays of probes can also be employed on the samples per se or on samples that have been subjected to RNA amplification. The RNA is typically found in the cell-free fraction of these fluids, although sloughing of the liver cells may also occur; in this case, isolation of the RNA prior to measurement would be required. The isolated mRNA may also be amplified. Northern blots of the cell-free fluids may also be used as well as Northern blots of isolated mRNA from cellular portions of the fluids. In general, these methods are less convenient than the measurement of protein if the measurement is not confined to the cell-free portion.

While individual markers may be used in the assay, more reliable results are obtained using a panel of two or more markers. Thus, combinations of the markers that are part of the present invention, such as ASGR1 plus FAH plus PIPOX or a combination of ASGR2 with PLG and MAT1A might be used. In addition, one or more of the markers of the invention may be used in combination with one or more known markers, such as LDH and ALT.

Thus, for example, ASGR1 may be coupled with any one of the remaining 13 markers, or any two of said remaining markers or any three of said remaining markers, any four of said remaining markers or any combination of up to 13 of said markers. The same is true for ASGR2 and each of the markers in the group of 14.

In addition, or instead, one or more known markers of liver injury may also be combined with any one or more of the markers of the invention. Thus, the assessment may include one or more of the newly discovered markers set forth herein in combination with one or more of the markers already known. The specificity and accuracy of the assessment is improved as the number of markers is increased. Thus, the assessment may include 1-20 or more markers in all, one of which at least must be one of the 14 novel markers set forth herein or any intermediate number may also be used, such as 5, 10, 12, or 16. In one embodiment, two of the new markers set forth in the present application are used alone or in combination with one or several other markers some of which may be those already known in the art.

Depending on the number of markers used in the assay, it may be useful to construct a "fingerprint" characteristic of liver injury in general or of a particular type of liver injury. Such fingerprints may readily be stored on computer-readable medium, and compared among individuals to construct a particularly incisive diagnostic when data from a multiplicity of individuals of various types of liver injury are compiled. The invention also includes a computer-readable medium which contains a multiplicity of such fingerprints.

The diagnoses and prognoses of the invention require comparison of the concentrations of the markers with those in normal subjects. The values for normal subjects can be determined by using a control subject, as would be typical in the case of laboratory determinations, where the analysis is carried out under the same conditions. In the case of human patients, a more common determination is a statistical combination of the results from a multiplicity of normal individuals.

The following examples are offered to illustrate but not to limit the invention.

Example 1

Selection of Candidate Markers

The choice of candidate markers for possible analysis was based on the assumption that proteins highly expressed in liver but generally not in other tissues that feed into the circulatory system would be specific indicators of liver injury when these highly expressed proteins are secreted into the blood due to the injury. Accordingly, information concerning the transcriptome of various normal tissues both at an mRNA level and a protein level was obtained and shown in FIG. 1. As shown in FIG. 1, the difference of expression level in liver is compared to the expression level of the highest level in any other tissue besides liver (normalized to z-scores). Hence, positive means that expression in liver is highest as compared to any tissue for the transcripts in the data set. The color key shows the positive or negative value for each gene listed on the right as determined in a particular dataset shown at the top. The data sets are as follows:

Hs_MPSS: Human MPSS
Hs_GNF: Human GNF
Hs_EST: Human EST
Mm_MPSS_m: Male mouse MPSS
Mm_MPSS_f: Female mouse MPSS
Mm_GNF: Mouse GNF
Mm_EST: Mouse EST MPSS: Massively Parallel Signature Searching, GNF: Novartis Research Foundation microarrays, and EST: NCBI Expressed Sequence Tag database.

The human MPSS dataset was generated from 34 human normal tissues MPSS using data obtained by ISB. Mouse MPSS datasets were generated from male and female 87 normal tissue samples from the MPSS Mouse Transcriptome Analysis Project of the NCBI. Human and mouse GNF datasets are from the Human and Mouse GeneAtlas GNF, gcRMA dataset of 79 human samples and 122 mouse samples obtainable from symatlas.gnf.org/SymAtlas/. The human and mouse EST datasets were obtained from UniGene dataset at NCBI. In order to make it possible to compare data from these three totally different platforms, meta-analysis was used to normalize expression values to z-scores over all samples in each dataset.

Example 2

Protein Analysis

To confirm usefulness as markers, the levels of various proteins indicated promising from FIG. 1 were analyzed among 16 normal human tissues, including liver, with the results shown in FIG. 2. According to FIG. 2, BHMT, ALDH1L1, FTCD and MAT1A specific for liver as are CPS1, FAH, GNMT and others. HAO1 and PIPOX also showed high levels in skeletal muscle. FBPI was found in the small intestine and COMT was found in the heart. Such non-specificity may not interfere with the use of these as markers, however. On the other hand, plasminogen and RBB4 were widely distributed and poorly expressed in liver.

Example 3

Murine Model

The effectiveness of various proteins as markers was tested by inducing liver damage in mice using acetaminophen and then assessing serum for various proteins by surface plasmon resonance (SPR) detection of complex formation with the relevant antibody and confirmed by Western blot. The known marker, AST, was used as a control.

Nine week old male C57BL6/J mice were fasted for 24 hours and then administered 300 mg/kg acetaminophen intraperitoneally. The mice were euthanized with $CO_2$ and whole blood was collected via cardiac puncture at various time intervals. The whole blood was incubated at 4° C. for 12 hours and centrifuged at 2,000 g for 10 minutes to obtain serum which was stored at −80° C. and then analyzed by SPR antibody array as described above and validated by Western blot. (The concentration of the known marker serum alanine amino transferase (AST) was determined by enzymatic assay.)

Figure 3:
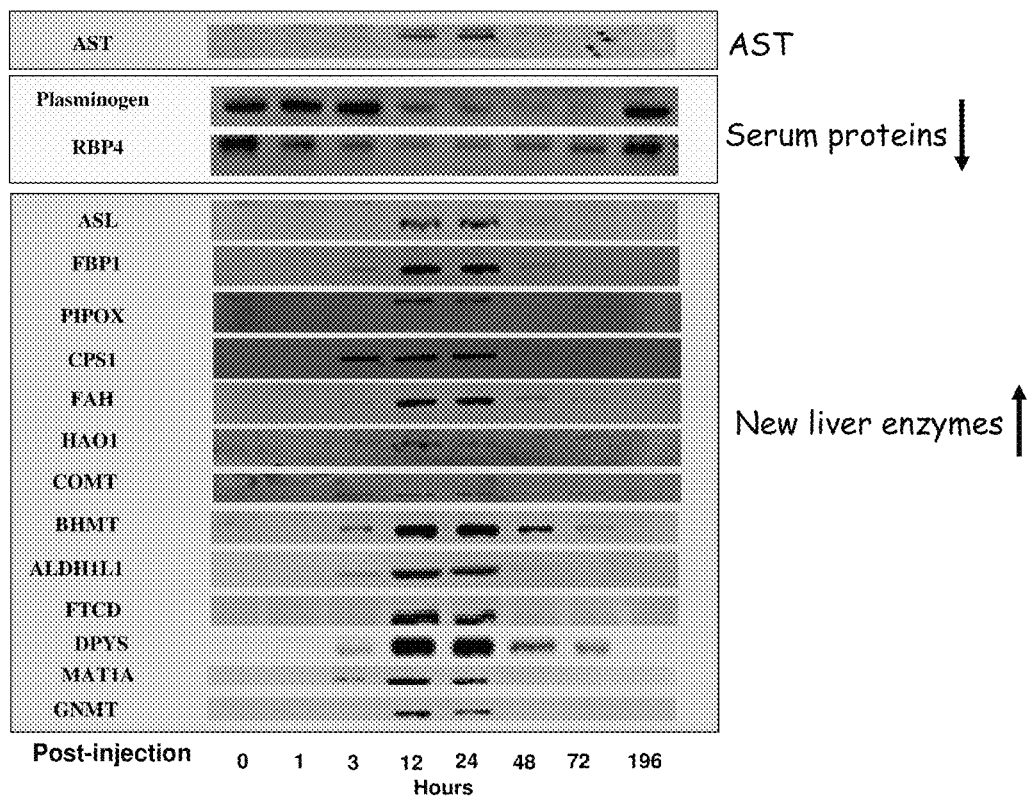
FIG. 3 shows the time course of the appearance of the biomarkers of the invention in serum of mice administered a toxic dose of acetaminophen.

The results are shown as the Western blot validations in FIG. 3. As shown, 12 markers whose plasma level increases in the event of liver injury were shown at elevated levels after 12-24 hours after which the levels in plasma declined. Both plasminogen and RBP4 showed a decrease in plasma levels at this time. The control AST showed corresponding increase in serum levels at the same time as the novel markers.

Example 4

Elevation of FAH in Human Patients with Liver Damage

Serum samples from patients with liver damage and from subjects with normal livers were analyzed by Western blot using detection with rabbit antihuman FAH polyclonal antibody and tested using the standard marker ALT (alanine transaminase). As shown in FIG. 4A, four patients with liver disease showed strong bands at 46 kDa using Western blot to detect FAH, essentially proportional to ALT levels determined in standard tests. Four control individuals had less FAH as well as diminished levels of ALT.

FIG. 4B shows the results obtained using the same two tests with two individuals, one of whom was recovering from liver injury, and the other who had liver cancer and eventually died. As shown in FIG. 4B, the level of FAH steadily diminished (as did the level of ALT) until recovery for the patient who was successfully treated, while the level of both FAH and ALT increased in the liver cancer patient until the day of death.

Additional confirmation was obtained using Western blot of human sera from a number of individuals, one of whom, A2, showed extensive liver damage. FBP1, DPYS, GST, and FAH were detectable in the serum of this patient, but not in normals.

The invention claimed is:
1. A kit for use in performing a method for detecting liver damage which kit comprises a panel of at least four protein-binding members, wherein each member is specifically reactive with one protein selected from the group consisting of asialoglycoprotein receptor 2 (ASGR2), 10-formyltetrahydro dehydrogenase (ALDH1L1), formiminotransferase cyclodeaminase (FTCD), catechol-O-methyltransferase (COMT), dihydropyrimidinase (DPYS), carbamoyl phosphate synthase (CPS1), fructose-1,6-bisphosphatase 1 (FBP1), fumarylacetoacetate hydrolase (FAH), glycine-N-methyltransferase (GNMT), 3-hydroxy-3-methylglutaryl-coenzyme A synthase 2 (HMGCS2), methionine adenosyltransferase 1 (MAT1A), plasminogen (PLG) and retinal binding protein 4 (RBP4);
wherein each protein binding member binds a different protein of said group; and reagents for detecting a complex formed between said member and said protein.

2. The kit of claim 1 wherein said members are antibodies and wherein said antibodies are displayed on a surface or in a microarray.

3. The kit of claim 1 wherein said at least four protein-binding members bind to at least four proteins selected from the group consisting of ASGR2, ALDH1L1, FTCD, COMT, DPYS, FBP1, FAH, GNMT, HMGCS2, MAT1A, PLG, and RBP4.

4. The kit of claim 1 wherein said at least four protein-binding members bind to at least four proteins selected from the group consisting of GNMT, CPS1, FAH, ALDH1L1, FTCD, MAT1A, and FBP1.

5. The kit of claim 1 wherein the panel contains at least 5 members.

6. The kit of claim 1 wherein the panel contains at least 6 members.

7. The kit of claim 1 wherein the panel contains at least 10 members.

8. The kit of claim 1 wherein the reagents permit detecting by surface plasmon resonance microarray, Western blot, or lateral flow assay.

9. The kit of claim 1 which further includes reagents for assessing the concentration of at least one known protein marker for liver damage selected from the group consisting of ALT, AST, ALP, GGT and LDH.

\* \* \* \* \*